(12) United States Patent
Hu et al.

(10) Patent No.: US 11,543,638 B2
(45) Date of Patent: Jan. 3, 2023

(54) DARK-FIELD MICROSCOPE APPARATUS UTILIZING PORTABLE ELECTRONIC COMMUNICATION DEVICE

(71) Applicants: Ye Hu, Scottsdale, AZ (US); Dali Sun, Tempe, AZ (US)

(72) Inventors: Ye Hu, Scottsdale, AZ (US); Dali Sun, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 401 days.

(21) Appl. No.: 16/637,733

(22) PCT Filed: Aug. 9, 2018

(86) PCT No.: PCT/US2018/046003
§ 371 (c)(1),
(2) Date: Feb. 7, 2020

(87) PCT Pub. No.: WO2019/032824
PCT Pub. Date: Feb. 14, 2019

(65) Prior Publication Data
US 2020/0183137 A1  Jun. 11, 2020

Related U.S. Application Data

(60) Provisional application No. 62/542,980, filed on Aug. 9, 2017.

(51) Int. Cl.
*G02B 21/00* (2006.01)
*G01N 21/51* (2006.01)
(Continued)

(52) U.S. Cl.
CPC ......... *G02B 21/0008* (2013.01); *G01N 21/51* (2013.01); *G01N 33/587* (2013.01);
(Continued)

(58) Field of Classification Search
CPC ............... G02B 21/00; G02B 21/0008; G02B 21/0016; G02B 21/0028; G02B 21/0032;
(Continued)

(56) References Cited

U.S. PATENT DOCUMENTS 5,024,513 A * 6/1991 Hayashi ................. G02B 21/24
359/384
5,497,267 A * 3/1996 Ishikawa .............. G02B 21/025
359/380

(Continued)

FOREIGN PATENT DOCUMENTS

CN          103054558 A     4/2013
CN          105579881 A     5/2016
(Continued)

OTHER PUBLICATIONS

Author Unknown, "Dark-field mobile phone microscope," Vimeo, Oct. 24, 2017, retrieved from the Internet: https://vimeo.com/239669463, 1 page.

(Continued)

*Primary Examiner* — Thong Q Nguyen
(74) *Attorney, Agent, or Firm* — Withrow & Terranova, P.L.L.C.; Vincent K. Gustafson

(57) ABSTRACT

A mobile phone-based dark field microscope (MDFM) apparatus suitable for quantifying nanoparticle signals is provided. The MDFM apparatus includes an electrically operated light source, a dark-field condenser, a slide housing configured to receive an analytical slide, and an adapter housing configured to receive an objective lens and receive a portable electronic communication device. The slide housing positions the analytical slide between the objective lens and the dark-field condenser. The adapter housing registers the objective lens with a camera lens of the portable electronic communication device. A method for performing a (Continued)

biological quantitative study using the dark-field microscope apparatus is further provided.

21 Claims, 9 Drawing Sheets

(51) Int. Cl.
- G01N 33/58 (2006.01)
- G02B 21/02 (2006.01)
- G02B 21/10 (2006.01)
- G02B 21/26 (2006.01)

(52) U.S. Cl.
CPC .......... G02B 21/025 (2013.01); G02B 21/10 (2013.01); G02B 21/26 (2013.01); G01N 2201/0221 (2013.01)

(58) Field of Classification Search
CPC ...... G02B 21/02; G02B 21/025; G02B 21/06; G02B 21/08; G02B 21/10; G02B 21/24; G02B 21/241; G02B 21/26; G02B 21/34; G02B 21/362; G02B 7/00; G02B 7/02; G02B 7/022; G02B 7/023; G02B 7/04
USPC .................................................. 359/368–398
See application file for complete search history.

(56) References Cited

U.S. PATENT DOCUMENTS

| | | | |
|---|---|---|---|
| 9,678,324 | B2 | 6/2017 | Yoshida |
| 10,281,369 | B2 * | 5/2019 | Wu .................... H01L 27/14643 |
| 2005/0018280 | A1 | 1/2005 | Richardson |
| 2006/0092504 | A1 | 5/2006 | Hayashi |
| 2012/0105949 | A1 | 5/2012 | Cummings et al. |
| 2015/0054935 | A1 | 2/2015 | Muramatsu |
| 2017/0160534 | A1 | 6/2017 | Fan |

FOREIGN PATENT DOCUMENTS

| | | |
|---|---|---|
| WO | 2013115217 A1 | 8/2013 |
| WO | 2017112957 A1 | 6/2017 |

OTHER PUBLICATIONS

Azzay, H.M.E. et al., "Clinical laboratory data: acquire, analyze, communicate, liberate," Clinical Chimica Acta, vol. 438, Aug. 27, 2014, Elsevier BV, pp. 186-194.

Extended European Search Report for European Patent Application No. 18845207.2, dated Mar. 29, 2021, 8 pages.

First Office Action for Chinese Patent Application No. 201880064554.4, dated Aug. 25, 2021, 7 pages.

Bogoch, I. et al., "Short Report: Mobile Phone Microscopy for the Diagnosis of Soil-TransmittedHelminth Infections: A Proof-of-Concept Study," The American Journal of Tropical Medicine and Hygiene, vol. 88, No. 4, 2013, The American Society of Tropical Medicine and Hygiene, pp. 626-629.

Breslauer, D.N. et al., "Mobile Phone Based Clinical Microscopy for Global Health Applications," PLoS One, vol. 4, Issue 7, Jul. 2009, 7 pages.

D'Ambrosio, M.V. et al., "Point-of-care quantification of blood-borne filarial parasites with a mobile phone microscope," Science Translational Medicine, vol. 7, Issue 286, May 6, 2015, American Association for the Advancement of Science, 10 pages.

Diederich, B. et al., "Using machine-learning to optimize phase contrast in a low-cost cellphone microscope," PLoS One, vol. 13, No. 3, Mar. 1, 2018, 20 pages.

Dong, S. et al., "FPscope: a field-portable high-resolution microscope using a cellphone lens," Biomedical Optics Express, vol. 5, No. 10, Oct. 1, 2014, Optical Society of America, 6 pages.

Hu, Y. et al., "Nanodevices in diagnostics," WIREs Nanomediciting and Nanobiotechnology, vol. 3, Issue 1, Jan./Feb. 2011, John Wiley & Sons, Inc., pp. 11-32.

Kobori, Y. et al., "Novel device for male infertilityscreening with single-ball lens microscope and smartphone," Fertility and Sterility, vol. 106, Issue 3, 2016, Elsevier Inc., 5 pages.

Lee, S.A. et al., "A smartphone-based chip-scale microscope using ambient illumination," Lab on a Chip, vol. 14, 2014, Royal Society of Chemistry, 9 pages.

Phillips, Z. et al., "Multi-Contrast Imaging and Digital Refocusing on a Mobile Microscope with a Domed LED Array," PLoS One, vol. 10, No. 5, May 13, 2015, 13 pages.

Skandarajah, A. et al., "Quantitative Imaging with a Mobile Phone Microscope," PLoS One, vol. 9, Issue 5, May 2014, 12 pages.

Sun, D. et al., "A noise reduction method for quantifying nanoparticle light scattering in low magnification dark-field microscope far-field images," Author Manuscript, Analytical Chemistry, vol. 88, No. 24, Dec. 2016, 12 pages.

Switz, N.A. et al., "Low-Cost Mobile Phone Microscopy with a Reversed Mobile Phone Camera Lens," PLoS One, vol. 9, Issue 5, May 2014, 7 pages.

Walzik, M. et al., "A portable low-cost long-term live-cell imaging platform for biomedical research and education," Biosensors and Bioelectronics, vol. 64, 2015, Elsevier B.V., pp. 639-649.

International Search Report and Written Opinion for International Patent Application No. PCT/US2018/046003, dated Oct. 30, 2018, 12 pages.

International Preliminary Report on Patentability for International Patent Application No. PCT/US2018/046003, dated Feb. 20, 2020, 10 pages.

* cited by examiner

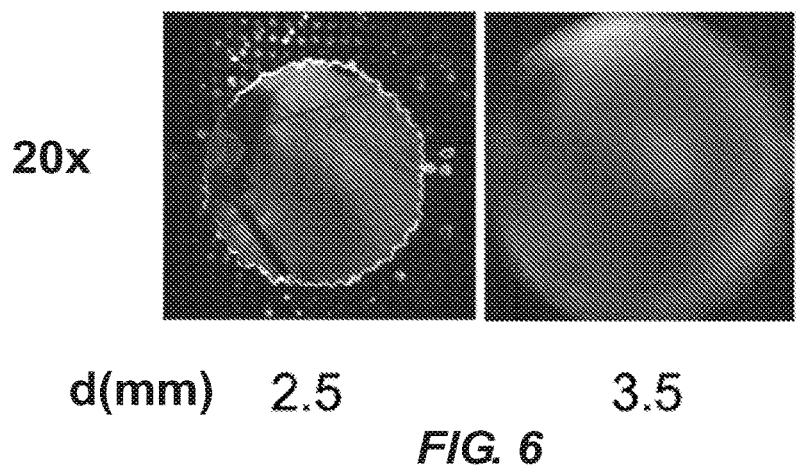
FIG. 6
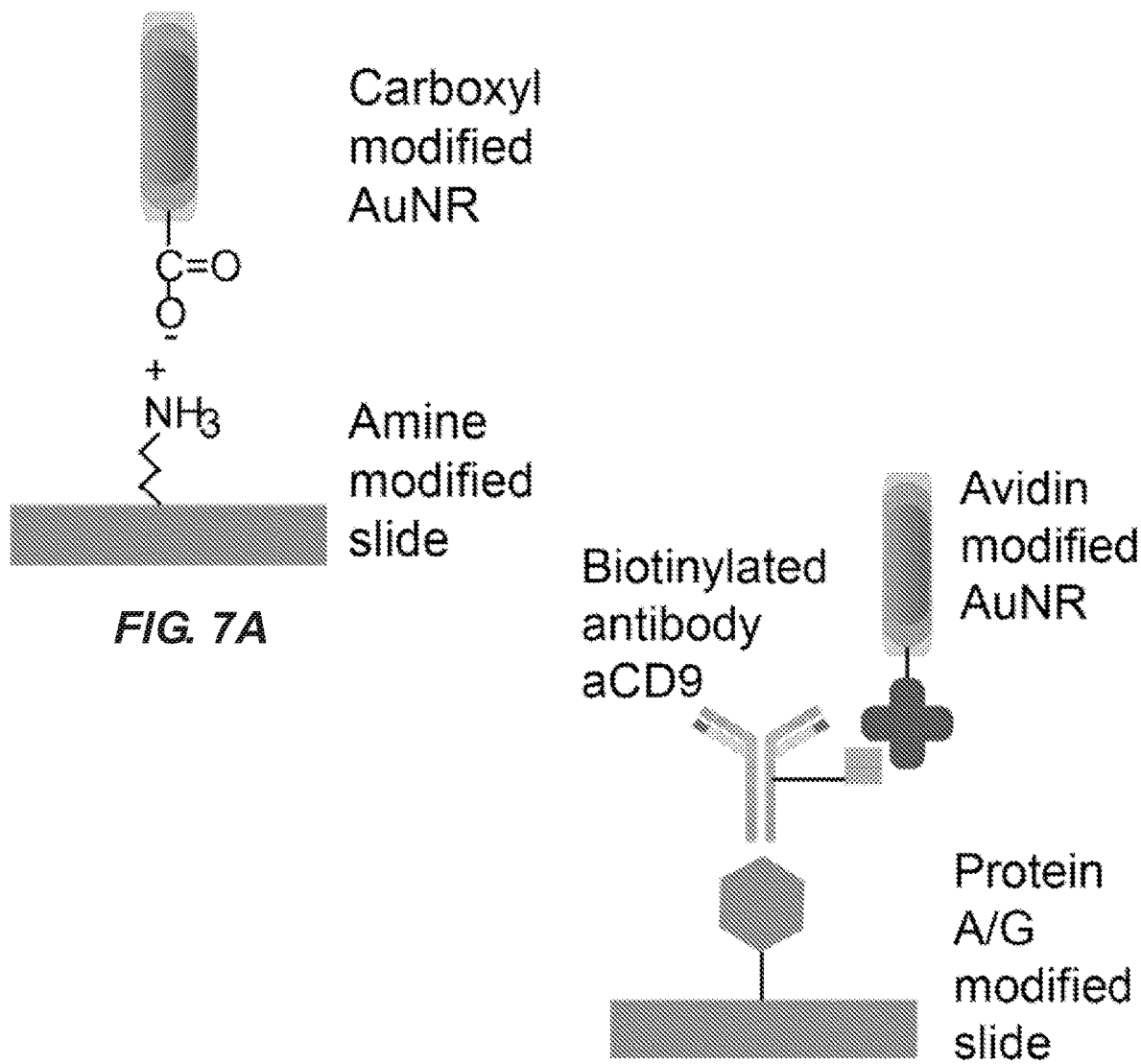
FIG. 7A
FIG. 8A

Table 2. Sensitivity of the quantitative assays

| Assay | (ng/µL) | MDFM | DDFM |
|---|---|---|---|
| Binding affinity | LOD | 4.6 | 0.6 |
|  | LOQ | 15.3 | 2.1 |
| Protein quantification | LOD | 135.2 | 30.1 |
|  | LOQ | 811.3 | 180.9 |

LOD: Limit of detection; LOQ: limit of quantitation

FIG. 9

Table 1. Differences of the mobile and desktop DFM systems.

|  | Mobile DFM | Desktop DFM |
|---|---|---|
| Light source | 3 LEDs (1,000 lux) | Halogen lamp (> 10,000 lux) |
| Camera model | Motorola XT1064 | Olympus DP71 |
| Maximum resolution | 3264 × 2448 JPEG (8.0 megapixels) | 4080 × 3072 (12.5 megapixels) |
| Camera sensor | CMOS | CCD |
| Weight | 0.38 kg | 26 kg |
| System cost with lens | $1,360 (10×) / $1,560 (20×) Motorola Moto G2* | >$50,000 Olympus IX81 |

FIG. 10

DARK-FIELD MICROSCOPE APPARATUS UTILIZING PORTABLE ELECTRONIC COMMUNICATION DEVICE

STATEMENT OF RELATED APPLICATIONS

This application is a 35 U.S.C. § 371 national phase filing of International Application No. PCT/US2018/046003 filed Aug. 9, 2018, and claims priority to U.S. Provisional Patent Application No. 62/542,980 filed Aug. 9, 2017, wherein the entire contents of the foregoing applications are hereby incorporated by reference herein.

GOVERNMENT RIGHTS IN INVENTION

This invention was made with government support under R01 AI113725 and R01 AI122932 awarded by the National Institutes of Health. The government has certain rights in the invention.

TECHNICAL FIELD

The present disclosure relates to dark-field microscope apparatuses and methods of performing biological quantitative studies utilizing such apparatuses, including (but not limited to) dark-field microscope apparatuses and methods suitable for quantifying nanoparticle signals that may be generated with nanoparticles providing scatter signals (e.g., gold or silver nanoparticles such as nanorods).

BACKGROUND

Gold nanoparticles have become prevalent labeling agents for detection and quantification of different targets, cellular imaging, biomolecular quantification, and performance of interaction studies. Conventional studies utilizing gold nanoparticles rely on complex equipment that limits their applicability to field settings. Portable spectrometry has been nominated as a potential solution for nanoparticle quantification; however, it suffers from complex setup requirements as well as either low throughput or low sensitivity. Nanoparticle-based lateral-flow chromatographic immunoassays are point-of-care devices, but usually are not quantitative, and require extensive development and validation.

Nanoparticle-based variants of standard immunoassays have potential as quantitative point-of-care immunoassays, since antibody-linked nanoparticle probes can be stored dry at ambient temperature (unlike enzyme-linked antibodies used in conventional immunoassays, which require low temperature storage).

Dark-field microscopy (also known as "dark-ground microscopy") describes microscopy methods that exclude the unscattered beam from the image. As a result, the field around the specimen (i.e., where there is no specimen to scatter the beam) is generally dark. Dark-field microscope (DFM) image analysis is commonly used to sensitively detect and precisely quantify nanoparticle-based immunoassay variants. The pairing of DFM image analysis and nanoparticles has resolved many critical quantification problems in bioresearch and clinical practice. DFM image analysis requires a high-magnification microscope, since low-magnification (far-field) DFM images are highly sensitive to surface artifacts and debris that can easily mask nanoparticle signals. The size, cost, and delicate character of conventional DFM systems limit their utility in non-laboratory settings—such as field hospitals and other settings, in which these factors represent barriers to their use. In addition to their lack of portability, conventional DFM systems may also be limited in terms of their ease of use.

Attempts to develop more portable DFM approaches date back to 1958, when dermatologists utilized DFM image analysis to diagnose agents responsible for multiple diseases (including syphilis) that produced skin lesions, but these devices fell out of use upon the development of other technologies, and few advances in DFM image analysis have been made since that time.

Recent technology advances driven largely by mobile phone camera development have spurred the use of mobile phone cameras in medical applications, including portable microscopy for numerous point-of-care diagnostics. As of the effective date of this application, however, Applicant is unaware of any far-field DFM system incorporating a mobile phone camera.

SUMMARY

Disclosed herein is a mobile phone-based DFM (MDFM) apparatus suitable for quantifying nanoparticle signals for a variety of research and medical applications. Such apparatus is lightweight and portable in character. In certain embodiments, a MDFM apparatus uses an inexpensive triple-LED light source, a standard dark-field condenser, an objective lens (e.g., 20× magnification, 10× magnification, or any other suitable magnification), and structural elements (e.g., one or more housings) configured to mate these components to a mobile phone camera. MDFM apparatuses disclosed herein are compatible with high throughput assays, and provide robust sensitivity, stability, and reproducible results with simple setup. Such apparatuses may provide a valuable platform for the practice of nanotechnology in field settings and other resource-limited environments.

In one aspect, the present disclosure relates to a dark-field microscope apparatus including: an adapter housing, an electrically operated light source, a dark-field condenser, and a slide housing. The adapter housing is configured to receive a portable electronic communication device and an objective lens, and to cause the objective lens to be registered with a camera lens of the portable electronic communication device when the portable electronic communication device is received by the adapter housing. The dark-field condenser is configured to condense light emissions generated by the electrically operated light source. The slide housing is configured to receive at least a portion of an analytical slide and position the analytical slide between the dark-field condenser and the objective lens.

In another aspect, a biomolecule quantification device comprises the dark-field microscope apparatus as disclosed herein, wherein the analytical slide is received by the slide housing, and the analytical slide contains at least one nanoparticle-based biomarker. In certain embodiments, the at least one nanoparticle-based biomarker comprises at least one gold or silver nanoparticle.

In another aspect, a method for performing a biological quantitative study utilizes a dark-field microscope apparatus as disclosed herein. The method includes: inserting at least a portion of the analytical slide into the slide housing to position the analytical slide between the dark-field condenser and the objective lens, wherein the analytical slide comprises at least one biomolecule and at least one nanoparticle-based biomarker; transmitting light emissions generated by the electrically operated light source through the dark-field condenser to impinge condensed light emissions on a target region of the at least a portion of the analytical slide; and generating a magnified image of the target region using the objective lens and the portable electronic communication device received by the adapter housing.

In another aspect, the present disclosure relates to a dark-field microscope apparatus including: an objective lens; a light source; a dark-field condenser configured to condense light emissions generated by the light source; a slide housing configured to receive an analytical slide and position the analytical slide between the dark-field condenser and the objective lens; and an adapter housing configured to receive a portable electronic communication device and to receive the objective lens, and configured to register the objective lens with a camera lens of the portable electronic communication device.

In another aspect, the present disclosure relates to a nanoparticle quantification device comprising a dark-field microscope apparatus as disclosed herein, wherein the analytical slide is received by the slide housing, and at least one type of nanoparticle is supported on or above a surface of the analytical slide.

In another aspect, the present disclosure relates to a biomolecule quantification device comprising a dark-field microscope apparatus as disclosed herein, wherein the analytical slide is received by the slide housing, and at least one nanoparticle-conjugated biomarker and a corresponding binding target are supported on or above a surface of the analytical slide.

In another aspect, the present disclosure relates to a method for performing a biological quantitative study utilizing a dark-field microscope apparatus as disclosed herein, the method comprising: inserting at least a portion of the analytical slide into the slide housing to expose an area of interest of the analytical slide to an optical path between the dark-field condenser and the objective lens, wherein the area of interest of the analytical slide contains target biomolecules and labels embodying conjugated nanoparticles comprising binding counterparts for the target biomolecules; transmitting light emissions generated by the light source through the dark-field condenser to impinge condensed light on the area of interest on the analytical slide; and generating a magnified image of the area of interest on the analytical slide using the objective lens and the portable electronic communication device received by the adapter housing.

In another aspect, the present disclosure relates to a method for diagnosing a disease, the method comprising: inserting at least a portion of an analytical slide into the slide housing of a dark-field microscope apparatus as disclosed herein to expose an area of interest of the analytical slide to an optical path between the dark-field condenser and the objective lens, wherein the area of interest of the analytical slide contains target biomolecules and labels embodying conjugated nanoparticles comprising binding counterparts for the target biomolecules; transmitting light emissions generated by the light source through the dark-field condenser to impinge condensed light on the area of interest on the analytical slide; generating a magnified image of the area of interest on the analytical slide using the objective lens and the portable electronic communication device received by the adapter housing; and analyzing the magnified image.

In another aspect, any one or more aspects or features described herein may be combined with any one or more other aspects or features for additional advantage.

Other aspects and embodiments will be apparent from the detailed description and accompanying drawings.

Those skilled in the art will appreciate the scope of the present disclosure and realize additional aspects thereof after reading the following detailed description of the preferred embodiments in association with the accompanying drawing figures.

BRIEF DESCRIPTION OF DRAWINGS

FIG. 6 shows two MDFM images captured with a 20× objective lens at 2.5 mm and 3.5 mm working distances, FIG. 7A is a schematic view of a binding affinity assay scheme involving binding between a carboxyl-acid functionalized gold nanorod (AuNR) and an amine modified slide.

FIG. 8A is a schematic view of a protein quantification assay scheme involving quantification of a biotinylated antibody aCD9 tagged with an avidin modified gold nanoparticle (AuNR) and bound to a protein A/G modified slide.

FIG. 9 is a table identifying sensitivity (including limit of detection (LOD) and limit of quantitation (LOQ) values) for the binding affinity and protein quantification assays described in connection with FIGS. 7A to 8B.

FIG. 10 is a table comparing features of a MDFM system as disclosed herein and a DDFM system.

DETAILED DESCRIPTION

Figure 1:
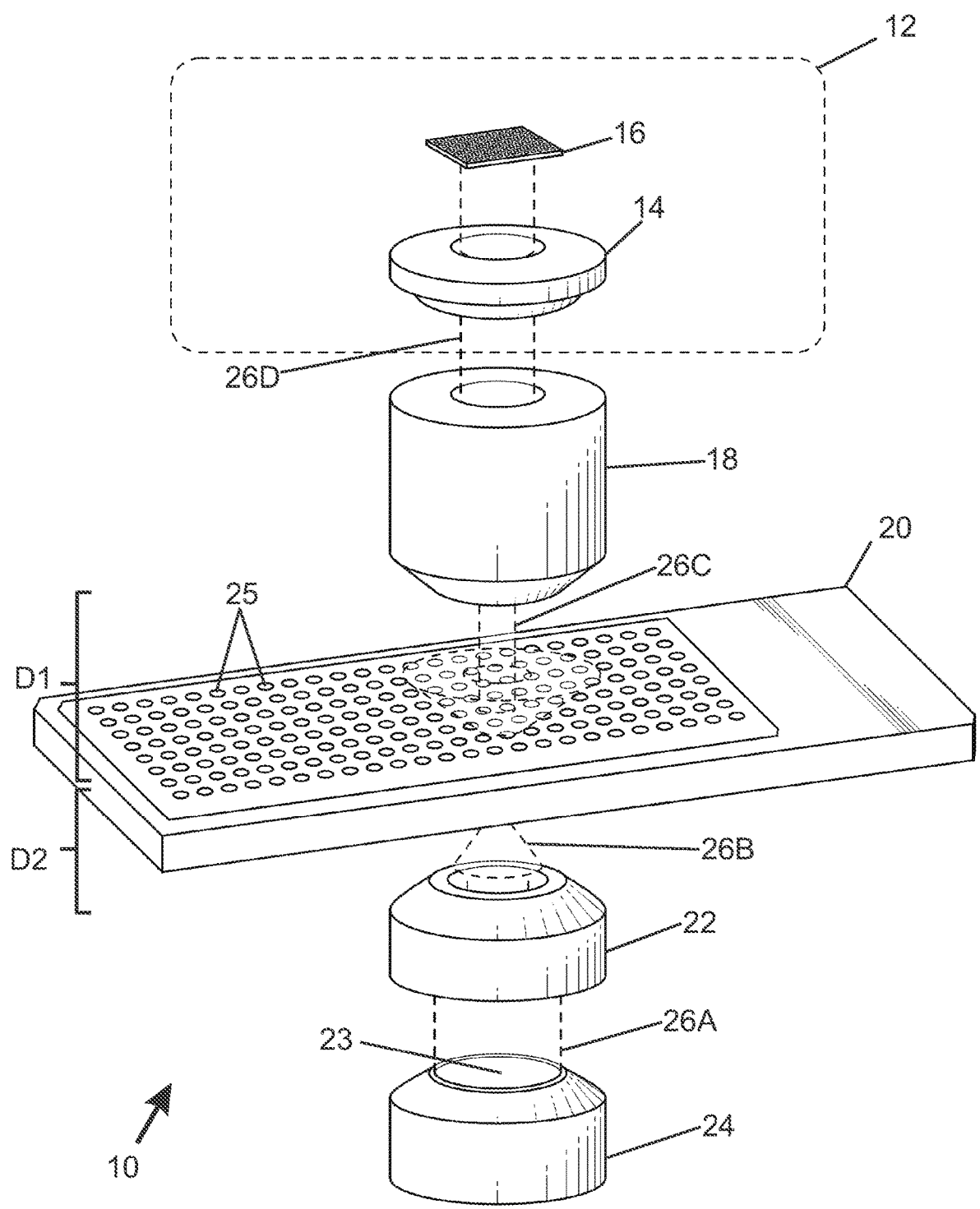
FIG. 1 is a schematic view of light interacting components of a dark-field microscope apparatus without illustration of an adapter housing or slide housing according to the present disclosure, showing passage of a light beam between the components.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element or region to another element or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Disclosed herein is a mobile phone-based DFM (MDFM) apparatus suitable for quantifying nanoparticle signals for a variety of research and medical applications. Such apparatus is lightweight and portable in character. In certain embodiments, a MDFM apparatus uses an inexpensive triple-LED light source, a standard dark-field condenser, an objective lens (e.g., 20× magnification, 10× magnification, or any other suitable magnification), and structural elements (e.g., one or more housings) configured to mate these components to a mobile phone camera. MDFM apparatuses disclosed herein are compatible with high throughput assays, and provide robust sensitivity and stability with simple setup, thereby providing a valuable platform for the practice of nanotechnology in field settings and other resource-limited environments.

Binding affinity and protein targeting studies conducted in parallel among MDFM apparatuses and desktop DFM systems validated the quantification capability of the proposed mobile MDFM platform. In certain embodiments, a MDFM apparatus may weigh less than about 400 g (e.g., about ~380 g) and cost less than $2000 including the mobile phone, while achieving performance analogous to that of a standard desktop dark-field microscope for quantifying target biomolecules in various assay schemes. MDFM apparatuses as disclosed herein allow stable, nanoparticle-based quantitation assays to be performed in resource-limited areas where standard assay approaches were previously impractical. In at least certain embodiments, MDFM apparatuses disclosed herein exhibit higher linearity, similar sensitivity, and similar stability in comparison to desktop DFM (DDFM) systems, and may be used in the performance of various bioassays, including high throughput assays and/or assays utilizing nanoparticle labeling. Analysis of images captured with MDFM apparatuses as disclosed herein reveal similar nanoparticle quantitation results to images acquired with a much larger and more expensive desktop DFM system.

Certain embodiments are directed to a dark-field microscope apparatus including: an adapter housing, an electrically operated light source, a dark-field condenser, and a slide housing. The adapter housing is configured to receive a portable electronic communication device and an objective lens, and to cause the objective lens to be registered with a camera lens of the portable electronic communication device when the portable electronic communication device is received by the adapter housing. The dark-field condenser is configured to condense light emissions generated by the electrically operated light source. The slide housing is configured to receive at least a portion of an analytical slide and position the analytical slide between the dark-field condenser and the objective lens. In certain embodiments, the adapter housing and the slide housing may be fabricated via three-dimensional printing, molding, machining, or other additive material addition and/or subtractive material removal processes. In certain embodiments, materials for fabricating the adapter housing and the slide housing may include one or more polymeric, metal, composite, and/or other materials. In certain embodiments, the adapter housing and the slide housing may comprise black acrylonitrile-butadiene-styrene (ABS) material. Preferably, the adapter housing and the slide housing are fabricated of materials sufficiently dimensioned to block transmission of ambient light.

Although the terms "MDFM" and "mobile phone dark-field microscope" are used in the present disclosure, it is to be appreciated that such apparatuses are not limited to the use of mobile phones, and may utilize various types of portable electronic communication devices that incorporate cameras—whether or not such devices necessarily embody mobile phones. For example, various tablet or tablet-like devices (e.g., Apple IPOD®, Apple IPAD®, and the like) that incorporate sophisticated cameras and processing capability, and are capable of WiFi communications without necessarily including cellular phone capability, may be used. Additionally, numerous types and brands of mobile phones incorporating cameras may be used, including various models produced by manufacturers such as (but not limited to) Apple, Samsung, Google, Huawei, ZTE, Lenovo, LG, Motorola, Sony, Nokia, and the like.

In one aspect, the present disclosure relates to a dark-field microscope apparatus including: an adapter housing, an electrically operated light source, a dark-field condenser, and a slide housing. The adapter housing is configured to receive a portable electronic communication device and an objective lens, and to cause the objective lens to be registered with a camera lens of the portable electronic communication device when the portable electronic communication device is received by the adapter housing. The dark-field condenser is configured to condense light emissions generated by the electrically operated light source. The slide housing is configured to receive at least a portion of an analytical slide and position the analytical slide between the dark-field condenser and the objective lens.

In certain embodiments, the adapter housing comprises a main body and a lens receiver that protrudes from the main body; the lens receiver is configured to receive the objective lens; and the slide housing is configured to receive at least portions of the lens receiver and the objective lens.

In certain embodiments, the main body comprises a support surface configured to abut a face of the portable electronic communication device, and the main body comprises at least one lateral wall configured to abut at least one lateral edge of the portable electronic communication device.

In certain embodiments, the slide housing comprises a bore; the lens receiver comprises a first outer wall configured to fit into a first portion of the bore; and the dark-field condenser comprises a second outer wall configured to fit into a second portion of the bore. In certain embodiments, the bore, the first outer wall, and the second outer wall may be generally tubular in shape. Such tubular shape may have a round, elliptical, square, or other suitable cross-section conformation in certain embodiments.

In certain embodiments, the dark-field microscope apparatus further includes: a first set screw configured to selectively promote engagement between the lens receiver and either (i) the slide housing or (ii) the objective lens, to adjust a first distance between the objective lens and the analytical slide; and a second set screw configured to selectively promote engagement between the slide housing and the dark-field condenser, to adjust a second distance between the dark-field condenser and the analytical slide.

In certain embodiments, at least one of the slide housing or the adapter housing is configured to permit a working distance between the objective lens and the analytical slide to be adjusted, and the dark-field microscope apparatus further comprises at least one locking element that is selectively operable to fix the working distance between the objective lens and the analytical slide.

In certain embodiments, the dark-field microscope apparatus further includes the objective lens. In certain embodiments, the objective lens, the slide housing, and the dark-field condenser are configured to form an optical path having a center aligned with an emissive center of the light source.

In certain embodiments, the slide housing defines at least one slot that is configured to receive at least a portion of the analytical slide. The slide housing is configured to permit the analytical slide to move relative to the slide housing to expose a different portion of the analytical slide to the optical path with each movement of the analytical slide.

In certain embodiments, the dark-field microscope apparatus further includes a base element configured to support the electrically operated light source and configured to receive an end portion of the slide housing.

In certain embodiments, the objective lens provides a magnification of at least 10 times. In certain embodiments, the objective lens is configured to provide variable magnification (i.e., multiple different magnifications).

In certain embodiments, the electrically operated light source comprises a solid state light source, such as a battery-powered solid state light source.

In certain embodiments, the electrically operated light source comprises at least one light emitting diode. In certain embodiments, the at least one light emitting diode is configured to generate a peak wavelength in the visible range.

In certain embodiments, the portable electronic communication device comprises a mobile phone.

In certain embodiments, the adapter housing and the slide housing each comprise at least one polymeric material.

In certain embodiments, the adapter housing and the slide housing are fabricated by three-dimensional printing.

In certain embodiments, the adapter housing and the slide housing are fabricated by molding.

In certain embodiments, the adapter housing and the slide housing are fabricated by a subtractive material removal process.

In another aspect, a biomolecule quantification device comprises the dark-field microscope apparatus as disclosed herein, wherein the analytical slide is received by the slide housing, and the analytical slide contains at least one nanoparticle-based biomarker. In certain embodiments, the at least one nanoparticle-based biomarker comprises at least one gold or silver nanoparticle.

In another aspect, a method for performing a biological quantitative study utilizes a dark-field microscope apparatus as disclosed herein. The method includes: inserting at least a portion of the analytical slide into the slide housing to position the analytical slide between the dark-field condenser and the objective lens, wherein the analytical slide comprises at least one biomolecule and at least one nanoparticle-based biomarker; transmitting light emissions generated by the electrically operated light source through the dark-field condenser to impinge condensed light emissions on a target region of the at least a portion of the analytical slide; and generating a magnified image of the target region using the objective lens and the portable electronic communication device received by the adapter housing.

In certain embodiments, the foregoing method may utilize one or more gold or gold-containing nanoparticles.

In another aspect, the present disclosure relates to a dark-field microscope apparatus including: an objective lens; a light source; a dark-field condenser configured to condense light emissions generated by the light source; a slide housing configured to receive an analytical slide and position the analytical slide between the dark-field condenser and the objective lens; and an adapter housing configured to receive a portable electronic communication device and to receive the objective lens, and configured to register the objective lens with a camera lens of the portable electronic communication device.

In certain embodiments, the objective lens, the slide housing, and the dark-field condenser are configured to form an optical path having a center aligned with an emissive center of the light source.

In certain embodiments, the slide housing defines at least one slot to receive the analytical slide; and the slide housing is configured to permit the analytical slide to move relative to the slide housing to expose a different portion of the analytical slide to the optical path with each movement of the analytical slide.

In certain embodiments, the dark-field microscope apparatus is configured to permit the objective lens to be swapped with a different objective lens to provide multiple different magnifications.

In certain embodiments, the objective lens is configured to provide variable magnification.

In certain embodiments, the objective lens comprises at least one lens providing a magnification value in a range of from 4 times to 100 times.

In certain embodiments, at least one of the slide housing or the adapter housing is configured to permit a working distance between the objective lens and the analytical slide to be adjusted. In certain embodiments, the dark-field microscope apparatus further includes at least one locking element that is selectively operable to fix the working distance between the objective lens and the analytical slide.

Exemplary MDFM Apparatus

FIG. 1 is a perspective schematic view of components of a MDFM apparatus 10 without illustration of an adapter housing or slide housing according to the present disclosure, according to one embodiment of the present disclosure. Various functional parts of the MDFM apparatus include a mobile phone 12 or other portable electronic communication device (which includes an integrated camera lens 14 and an imaging sensor 16), an objective lens 18, a dark-field condenser 22, and a light source 24, wherein a slide 20 including one or more sample-containing regions 25 may be positioned between the objective lens 18 and the dark-field condenser 22. In certain embodiments, the imaging sensor 16 may include a charge-coupled device (CCD) or a CMOS sensor. In certain embodiments, the light source 24 includes an emissive center 23 and may include one or more solid state emitters (e.g., light emitting diodes), and may be battery powered to facilitate portability of the MDFM apparatus 10. Emissions from the light source 24 form light a beam 26A that is transmitted through the dark-field condenser 22 to form a condensed light beam 26B that illuminates one or more portions of the slide 20 containing one or more samples in the sample-containing regions 25. Portions of the condensed light beam 26B that transit through the slide 20 and the sample(s) form an exit beam 26C that is focused by the objective lens 18 to form a focused exit beam 26D and received by the mobile phone 12 or other portable electronic communication device, with the focused exit beam 26D being transmitted through the integrated camera lens of 14 the mobile phone 12 to impinge on the imaging sensor 16. The integrated camera lens 14 of the mobile phone 12 may be fixed or variable in character. Although FIG. 1 does not illustrate an adapter housing or slide housing, and FIG. 1 shows various components as being spaced apart from one another (to permit illustration of passage of light through the components), it is to be appreciated than an operative MDFM apparatus may include an adapter housing and a slide housing, and components of the MDFM apparatus may be positioned much closer (or in contact with) one another, such as (but not limited to) a first distance D1 between the objective lens 18 and the analytical slide 20, and a second distance D2 between the dark-field condenser 22 and the analytical slide 20.

Figure 2A:
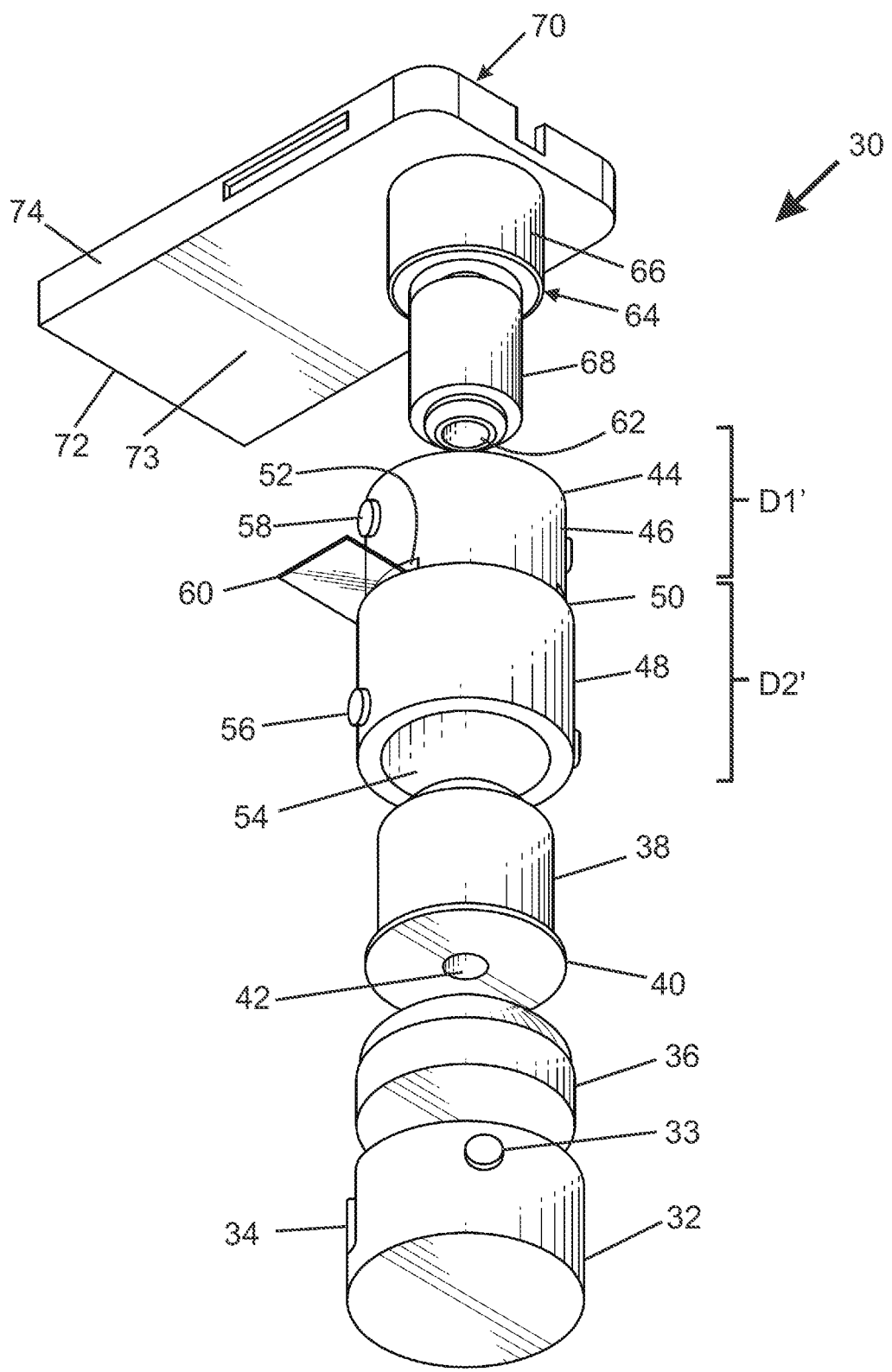
FIG. 2A is an exploded, lower perspective view of components of a mobile phone-based dark-field microscope (MDFM) apparatus according to one embodiment of the present disclosure.
Figure 2B:
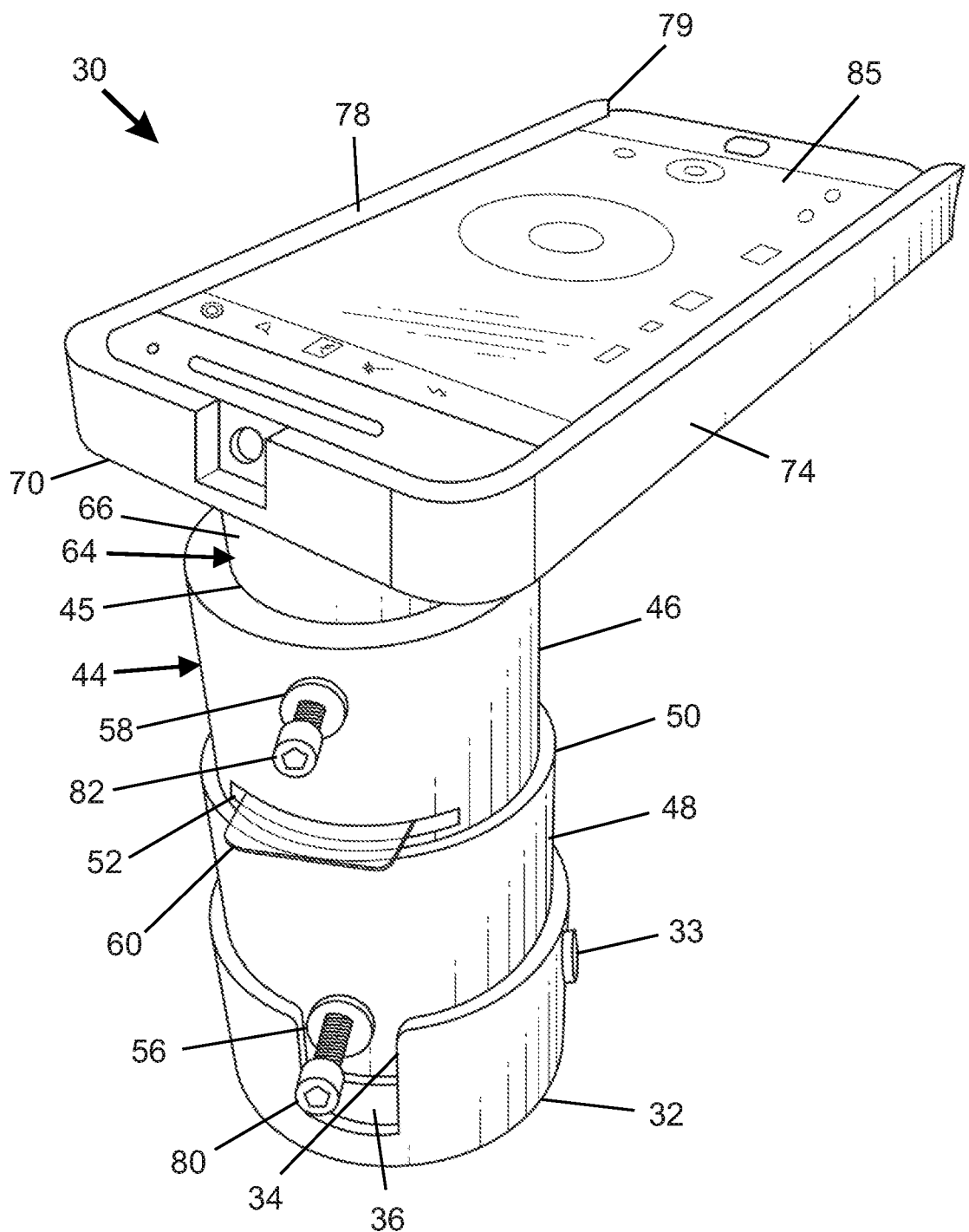
FIG. 2B is an upper perspective view of an assembled MDFM apparatus including the components shown in FIG. 2A, with a mobile phone received by the adapter housing.

FIG. 2A is an exploded perspective view illustration of components of a MDFM apparatus 30 according to one embodiment of the present disclosure. The MDFM apparatus 30 includes a base element 32, an electrically operated light source 36, a dark-field condenser 38, a slide housing 44 (having a generally cylindrical shape), an adapter housing 70, and an objective lens 62 received within a portion of the adapter housing 70. Starting at the bottom of the figure, FIG. 2A shows a generally cylindrical base element 32 configured to receive the electrically operated light source 36, which may include one or more LEDs optionally configured to generate a peak wavelength in the visible range. The base element 32 defines a vertical slot 34 that opens to a cylindrical cavity (not shown), and includes a lateral retention element 33 that may be used to promote retention of the slide housing 44 within a portion of the cavity of the base element 32. In one embodiment, the lateral retention element 33 includes a tapped (i.e., threaded) opening that may be configured to receive a threaded screw (not shown) that may be threaded through the tapped opening to selectively engage a cylindrical lower portion 48 of the slide housing 44 when the slide housing 44 is received by the base element 32. The dark-field condenser 38 includes a generally cylindrical body with a radially protruding lip 40 along a lower edge thereof. The dark-field condenser 38 also defines a lower aperture 42 configured to receive emissions of the electrically operated light source 36 when the dark-field condenser 38 is positioned above the light source 36. The dark-field condenser 38 is also configured to be received within a lower aperture 54 defined by the cylindrical lower portion 48 of the slide housing 44. The slide housing 44 defines at least one (e.g. horizontally arranged) slot 52 configured to receive an analytical slide 60. The slide housing 44 includes a cylindrical upper portion 46 and a cylindrical lower portion 48 with a shoulder 50 therebetween, with the lower portion 48 having a larger outer diameter than the upper portion 46. The upper portion 46 of the slide housing 44 defines an upper aperture (not shown) configured to receive at least a portion of the objective lens 62, which may also be received by a downwardly protruding, lower portion of an adapter housing 70 that embodies a lens receiver 64. The upper portion 46 of the slide housing 44 also includes a radially extending protrusion 58 that may include a tapped opening (not shown) for receiving a set screw (as shown in FIG. 2B). The lens receiver 64 of the adapter housing 70 includes a proximal portion 66 and a distal portion 68 that define a cavity which receives the objective lens 62. In certain embodiments, the proximal portion 66 has a larger diameter than the distal portion 68 of the lens receiver 64. In certain embodiments, the objective lens 62 provides at least 10× magnification (e.g., 10×, 15×, 20×, 25×, 30×, or some other desired magnification value, wherein in certain embodiments 4× or 8× magnification may be used). In certain embodiments, the objective lens 62 may include multiple lenses arranged in series. The adapter housing 70 is configured to receive a portable electronic communication device (e.g., a mobile phone) as well as the objective lens 62, and to cause the objective lens 62 to be registered with a camera lens of the portable electronic communication device when the portable electronic communication device is received by the adapter housing 70. The adapter housing 70 includes a main body 72 and the lens receiver 64 that protrudes downward from the main body 72. The main body 72 of the adapter housing 70 includes a support surface 73 configured to abut a face of the portable electronic communication device, and includes at least one lateral wall 74 configured to abut at least one lateral edge of the portable electronic communication device.

With continued reference to FIG. 2A, a lower portion of the slide housing 44 includes a radially extending protrusion 56 that is configured to be received by the vertical slot 34 defined in the base element 32. The radially extending protrusion 56 may further include a tapped (i.e., threaded) opening configured to receive a set screw (such as shown in FIG. 2B) configured to set a relative position between the slide housing 44 and the dark-field condenser 38, whereby manual movement between the slide housing 44 and the dark-field condenser 38, and selective engagement therebetween using a set screw, permits adjustment of a distance D2' between the dark-field condenser 38 and the analytical slide 60. The cylindrical upper portion 46 of the slide housing 44 includes a sidewall defining a tapped (i.e., threaded) opening configured to receive another set screw (shown in FIG. 2B) configured to selectively promote engagement between the lens receiver 64 and the slide housing 44, whereby manual movement between the lens receiver 64 and the slide housing 44, and selective engagement therebetween using a set screw, permits adjustment of a distance D1' between the objective lens 62 and the analytical slide 60 received by the slot 52 defined in the slide housing 44.

FIG. 2B is a perspective view photograph of an assembled MDFM apparatus 30 incorporating the components illustrated in FIG. 2A, with a mobile phone 85 received by the adapter housing 70. As shown, the mobile phone 85 is arranged between lateral walls 74 and below an upper peripheral lip 78 of the adapter housing 70, which includes an open end 79 devoid of a sidewall to permit the mobile phone 85 to be laterally inserted into the adapter housing 70. FIG. 2B illustrates the slide housing 44 supported from below by the electrically operated light source 36 arranged within the base element 32, with a lower set screw 80 extending through a tapped opening defined in the radially extending protrusion 56 (which extends into the vertical slot 34 of the base element 32) of the cylindrical lower portion 48 to engage the dark-field condenser (not shown) within the lower cylindrical portion 48 of the slide housing 44. An analytical slide 60 is arranged within the slot 52 defined in the slide housing 44, just above the shoulder 50, which represents a transition between the cylindrical lower and upper portions 48, 46 of the slide housing 44. As shown, the lens receiver 64 is received within an aperture 45 defined in the slide housing. FIG. 2B also illustrates an upper set screw 82 extending through a tapped opening in a radially extending protrusion 58 (positioned along the cylindrical upper portion of the slide housing 44) to engage the proximal portion 66 of the lens receiver 64, to enable adjustment of relative position (and the distance D1') between the objective lens 62 and the analytical slide 60.

In certain embodiments, the adapter housing and/or the slide housing may each comprise at least one polymeric material. In certain embodiments, an opaque polymeric material such as ABS may be used. In certain embodiments, the adapter housing and/or the slide housing may be fabricated of metal and/or composite materials. In certain embodiments, various manufacturing techniques such as three-dimensional printing (or another additive manufacturing process), molding (e.g., injection molding), and/or subtractive material removal (e.g., machining) may be used.

In certain embodiments, a biomolecule quantification device comprises the dark-field microscope apparatus as disclosed herein, wherein the analytical slide is received by the slide housing, and the analytical slide contains at least one nanoparticle-based biomarker. In certain embodiments, the at least one nanoparticle-based biomarker comprises at least one gold or silver nanoparticle.

In certain embodiments, a method for performing a biological quantitative study utilizes a dark-field microscope apparatus as disclosed herein. The method includes: inserting at least a portion of the analytical slide into the slide housing to position the analytical slide between the dark-field condenser and the objective lens, wherein the analytical slide comprises at least one biomolecule and at least one nanoparticle-based biomarker; transmitting light emissions generated by the electrically operated light source through the dark-field condenser to impinge condensed light emissions on a target region of the at least a portion of the analytical slide; and generating a magnified image of the target region using the objective lens and the portable electronic communication device received by the adapter housing.

To fabricate an exemplary MDFM apparatus, Solid-Works® 2013 CAD software (Dassault Systemes Solid-Works Corporation) was used to design the adapter housing and slide housing shown in FIGS. 2A and 2B. Such housings were fabricated with black acrylonitrile-butadiene-styrene (ABS) using a 3D printing service (3D hubs).

Image Capture and Processing

To provide a basis for comparison, DDFM images were acquired under consistent lighting and magnification using an Olympus IX81 microscope equipped with a dark-field condenser, a 4× or 10× magnification objective lens, and an Olympus DP71 digital camera, using a 1/45s exposure time. MDFM images using the apparatus described in connection with FIGS. 2A and 2B were acquired using a Motorola Moto G2 camera to capture images from a slide holder case containing a dark-field condenser and a 10× or 20× magnification objective lens and illuminated with a constant triple-LED white light source (Modgy, Inc.). Characteristics and components of the DDFM system and MDFM apparatus are disclosed and compared in tabular form in FIG. 10.

All images were processed and quantified using a "Dark-ScatterMaster" DFM algorithm using the following software input parameters: contour threshold (Ct)=253.020, center scale (S)=0.8, type=Red, Low (Lt)/High (Ht) quantification limit: 0/62. Motorola Moto G2 (XT1068) images of the MDFM apparatus were captured with a 1/15 s exposure time with Open Camera (Version 1.32.1) using an ISO 5000 configuration and allowing autofocus and 4× digital zoom. Magnification (M) was defined as the sample image height ($h_i$) divided by the height of the sample object ($h_o$), where $h_o$ was the target well diameter (1.5 mm) and $h_i$ was the diameter of the image in pixels multiplied by the resolution of the sensor chip (72 vs. 432 pixels/inch for MDFM and DDFM, respectively).

Binding Affinity Assay

Carboxyl-functionalized gold nanorods ("AuNRs") (C12-25-650-TC-50, Nanopartz) were activated to covalently bond amine groups by mixing 40 μL of AuNR ($4.22\times10^{12}$/mL) with 20 μL of EDC/NHS-sulfo phosphate buffered saline ("PBS") (2 mg/mL of 1-ethyl-3-(3-dimethylaminopropyl) carbodiimide hydrochloride and 1 mg/mL of N-hydroxysulfosuccinimide (Sigma-Aldrich) for 10 minutes at 25° C. These amine-reactive AuNRs were then PBS-washed and 1 μL of indicated AuNR concentrations were applied to replicate wells on 192-well amine-functionalized slides ($2\times10^{12}$ group/mm2, Arrayit), which were sonicated (Q500 Sonicator, Qsonica) for 8 minutes at 80% amplitude using a 5 second on/off cycle to accelerate hybridization. Slides were then washed for 10 min at 25° C. with 0.01% Tween-20 in PBS (PBST, pH 7.0), washed with deionized water, and then air-dried for DFM imagery. Binding affinity was calculated using nonlinear curve fitting with Origin 2015 software (OriginLab Corporation).

Protein Quantification Assay

Protein A/G-modified 192-well slides (Arrayit) were blocked with 1 μL/well Pierce Protein-Free Blocking Buffer (Thermo Scientific) for 1 hour at 25° C., then incubated with the indicated amounts of biotinylated CD9 antibody (NB110-81616, Novus) for 1 hour at 25° C., and PBS-washed for 10 min at 25° C. before hybridization with AuNR. Neutravidin-functionalized AuNR (Nanopartz C12-25-650-TN-50, $7\times10^{-9}$ M) were PBS-diluted (40 μL AuNR to 200 μL PBS) after which 1 μL/well of AuNR was applied to replicate wells, which were sonicated (Q500 Sonicator, Qsonica) for 8 minutes at 80% amplitude using a 5 second on/off cycle to accelerate hybridization. After hybridization, slides were washed for 10 min at 25° C. with 0.01% Tween-20 in PBS (PBST, pH 7.0), and deionized water, and then air-dried for DFM imagery.

Data Analysis

Limits of detection (LOD) and quantification (LOQ) were defined as 3× and 10× the standard deviation of the assay blank, respectively. Assay precision was determined with five replicates of three samples analyzed in a single assay (intra-assay) or in three assays analyzed on three different days (inter-assay). Graphs were generated with Origin 2015 and Microsoft Excel.

Optical Design and Characterization

This hand-held device simply combined (i) a low-cost small triple LED light source (~1k lux), (ii) a dark-field condenser, (iii) a 20× or 10× magnification objective lens, and (iv) 3D printed housings (i.e., adapter housing and slide housing) to permit the preceding parts to interface with the mobile phone. To characterize the MDFM apparatus, we compared this apparatus with a standard DDFM system for imaging nanoparticles. Both systems used the same dark-field condenser, but differed in their light sources, objective lenses, cameras, and total system weight and cost.

Figure 3:
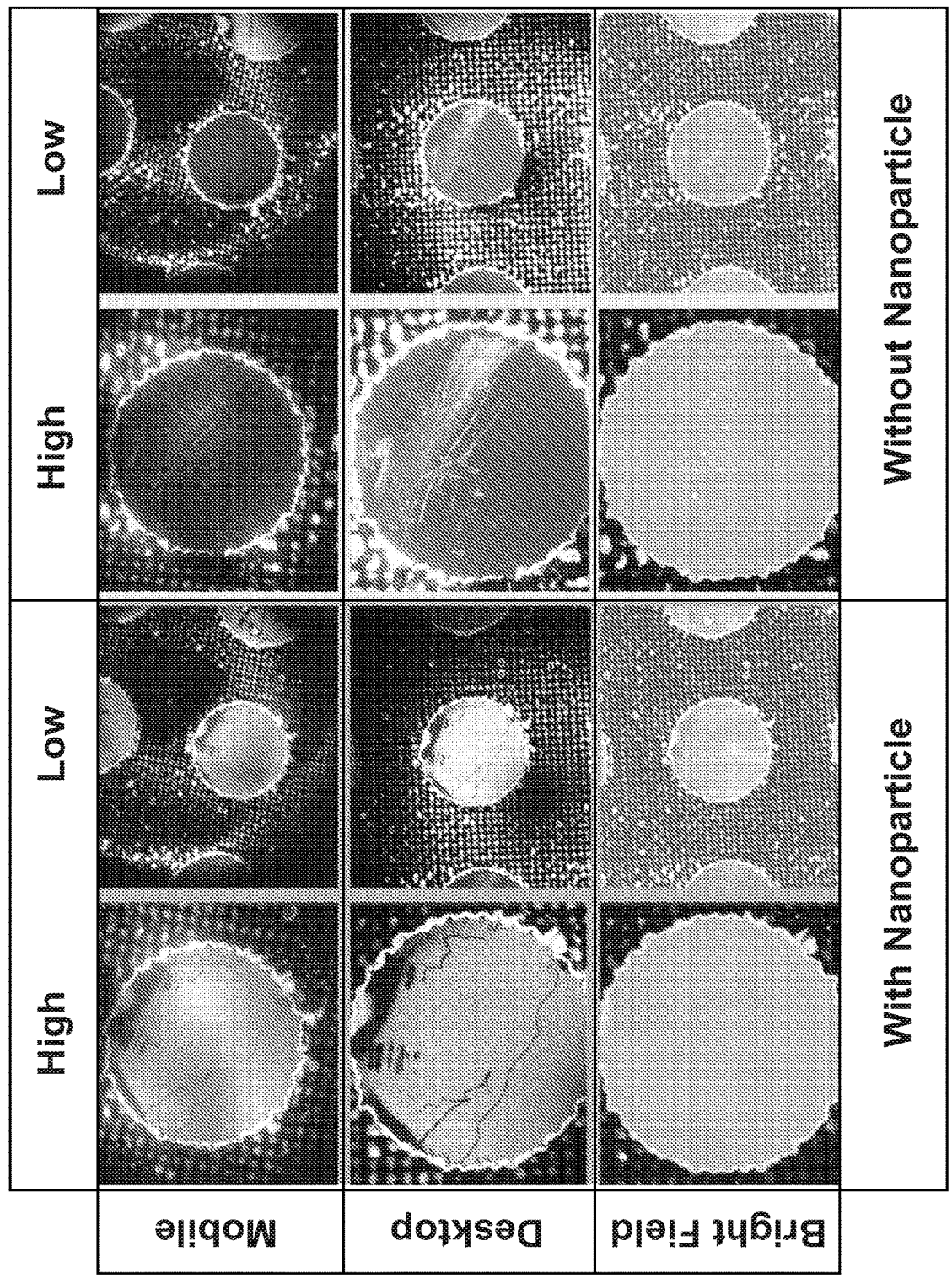
FIG. 3 provides a comparison of images obtained at high and low magnification for biological moieties with and without nanoparticles, respectively, obtained via a MDFM microscope system, a desktop dark-field microscope system (DDFM), and a bright field microscopy system, with 20× and 10× objective lenses employed for MDFM, and with 10× and 4× objective lenses employed for DDFM and bright field microscopy.

FIG. 3 provides a comparison of images obtained at high and low magnification for biological moieties with and without nanoparticles, respectively, obtained via MDFM, DDFM, and bright field microscopy, with 20× and 10× objective lenses employed for MDFM, and with 10× and 4× objective lenses employed for DDFM and bright field microscopy. Comparison of the image quality produced by these systems revealed that the MFDM images exhibited weaker and more uneven signals than the equivalent DDFM images, most likely due to their different lighting systems. The characterized MDFM apparatus employed a relatively weak (1,000-lux) triple-LED light source powered by a 3V lithium battery, as opposed to the DDFM system, which employed a single 100 W (>10,000-lux) halogen lamp. The MDFM light source was chosen for its low power draw and relatively high LED-based light output, but lighting artifacts associated with the MDFM images are consistent with the three point angular LED arrangement in the MDFM apparatus. The MDFM condenser, optimized for the DDFM system, may exacerbate these artifacts, as may the MDFM slide housing, which provides limited precision in aligning the condenser light path. MDFM image quality also suffers from the lower resolution of the MDFM CMOS vs. the DDFM CCD sensor (72 vs. 432 pixels/inch) at a given objective lens. Owing to these differences, different objective lenses were used for the MDFM apparatus (10× and 20× magnification) and DDFM system (4× and 10× magnification) in order to capture images at similar overall resolution. The low fixed aperture of the mobile phone camera (f/2) used by the MDFM apparatus also limits depth of focus, but this should not negatively influence surface-based imagery or biomarker quantification methods.

Functioning as a dark-field, the MDFM apparatus displays the nanoparticle on the surface similar to the DDFM system, as compared to the bright-field microscope, which was incapable of distinguish the nanoparticle at all. Despite advantages conferred by the more expensive DDFM system, the MDFM apparatus benefits from the low sensing resolution. The DDFM system with high resolution is more sensitive to surface scratch and debris, which negatively affect the nanoparticle quantification by imaging. The MDFM apparatus circumvented these noises by its inherently lower sensing resolution. Moreover, it was determined that a primary reason that the MDFM apparatus may be used for nanoparticle quantification is that the sensing resolution does not affect the quantification result. The magnification may sway the quantification slightly; however, experiments using DDFM under different resolutions revealed no significant quantification difference.

Figure 4:
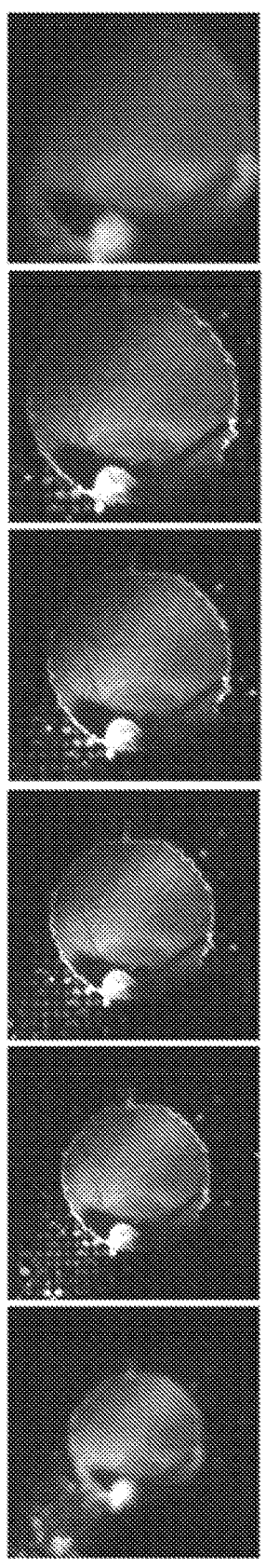
FIG. 4 shows six MDFM images captured with a 10× objective lens at different working distances of 1 mm, 3 mm, 5 mm, 7 mm, 9 mm, and 11 mm.
Figure 5:
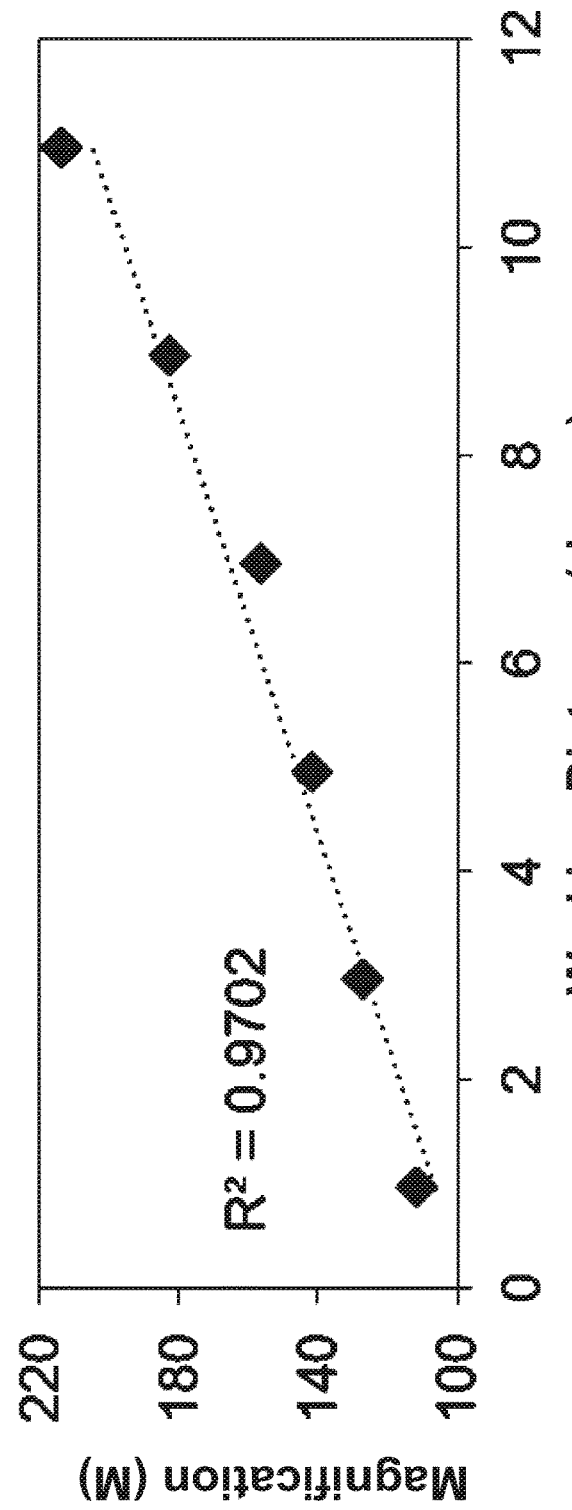
FIG. 5 is a plot of MDFM magnification (M) with a 10× objective lens versus working distance (d, mm), with a superimposed linear correlation plot and coefficient of determination ($R^2$) value.

Another beneficial feature of the MDFM apparatus is its autofocus function, which enabled focused 10× magnification DFM images to be captured over a relatively wide range of working distances (3 to 10 mm)—thereby reducing image capture time significantly and allowing the user to vary the size of the focused images. FIG. 4 shows six MDFM images captured with a 10× objective lens at different working distances of 1 mm, 3 mm, 5 mm, 7 mm, 9 mm, and 11 mm, indicating the autofocus limits of the mobile phone camera used with the MDFM apparatus. FIG. 5 is a plot of MDFM magnification (M) with a 10× objective lens versus working distance (d, mm), with a superimposed linear correlation plot and coefficient of determination ($R^2$) value. A high degree of linearity was shown. FIG. 6 shows two MDFM images captured with a 20× objective lens at 2.5 mm and 3.5 mm working distances, with the images being grayed to portray the focusing effect.

The MDFM apparatus did not exhibit dynamic working ranges when a 20× magnification objective lens was used, likely due to the more restricted working distance available for autofocus. By comparison, the DDFM system required precise manual adjustment to obtain focused images, with a set working distance and magnification available for each objective lens. The MDFM apparatus magnified samples 370-fold and 110- to 210-fold using 20× and 10× objective lenses, while the DDFM system magnified samples 375-fold and 150-fold using 10× and 4× objective lenses. After adjusting for lens and sensor differences, the respective focused high-power and low-power MDFM images exhibited magnifications corresponding to 98.7% and 58.6% to 112% of their matching DDFM images. It was therefore shown that the MDFM apparatus is capable of attaining similar magnification as the DDFM system, while exhibiting more flexibility with respect to the working distance, and enabling the user to more easily obtain focused images. The foregoing features represent significant advantages of a MDFM apparatus in a field setting.

FIG. 10 provides a table comparing features of an exemplary MDFM system as disclosed herein and a conventional DDFM system. The exemplary MDFM system may utilize a three-LED light source providing an aggregate output of about 1000 lux, as compared to the DDFM system that utilizes a halogen lamp providing an output of greater than 10,000 lux. The MDFM system may therefore utilize a light source utilizing less than about one tenth of the energy and generating less than about one tenth of the heat generated by a light source of a conventional DDFM system. The MDFM system may utilize a Motorola XT1064 camera providing 8.0 mexapixel resolution from a CMOS sensor versus an Olympus DP71 camera providing 12.5 megapixel resolution from a CCD sensor as utilized by a conventional DDFM system. The MDFM system may entail a total weight 0.38 kg and a total cost in a range of $1,360 to $1,560 (depending on the objective lens used), versus a total eight of 26 kg and a total cost in a range of $50,000. Clearly, the exemplary MDFM system entails dramatically lower cost and weight than to a conventional DDFM system.

Quantification for Bioassay

Figure 7B:
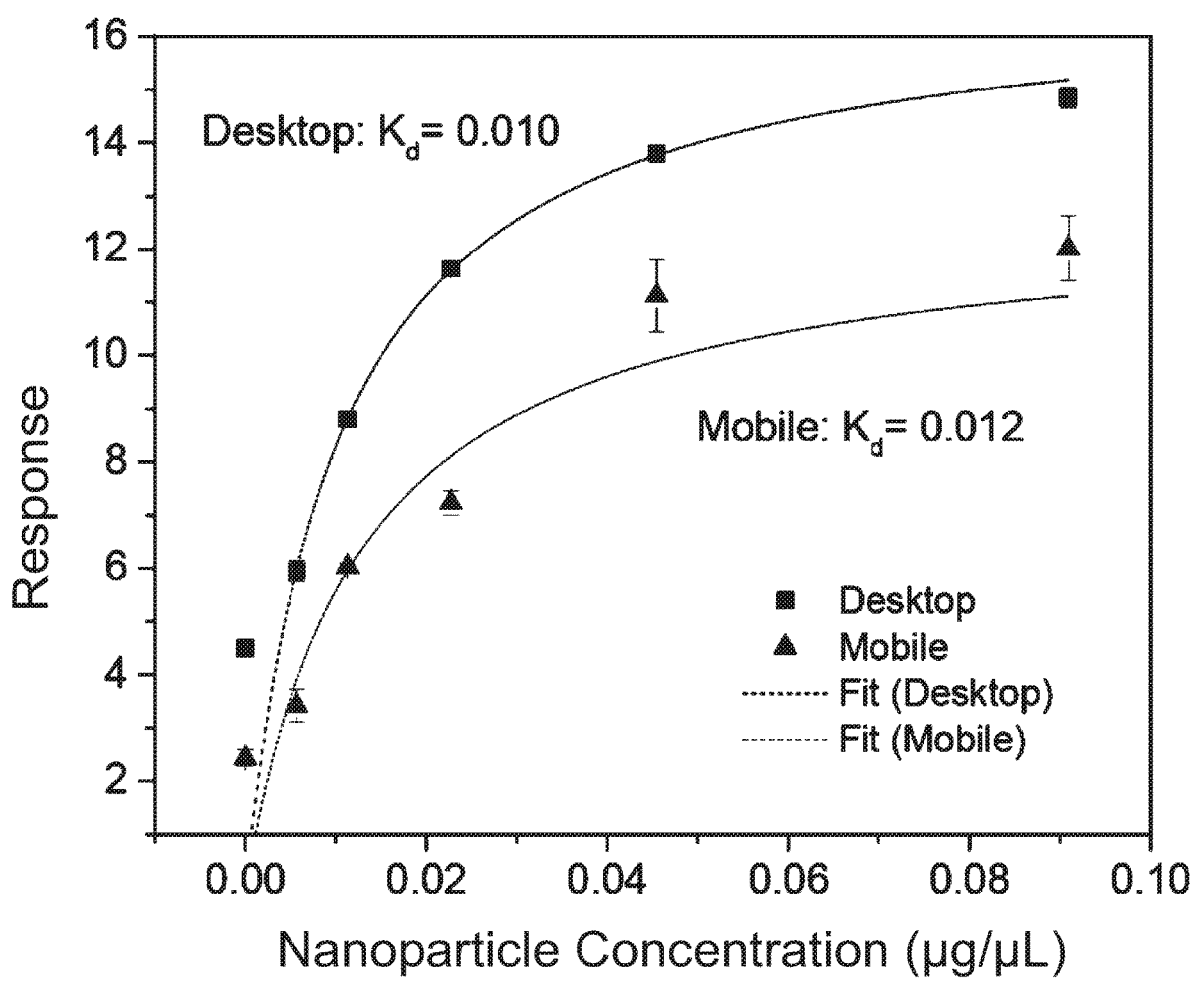
FIG. 7B provides superimposed plots of response versus nanoparticle concentration (μg/μL) for a binding affinity assay according to the scheme of FIG. 7A obtained using a MDFM apparatus as disclosed herein and a conventional DDFM system, with corresponding nonlinear fitted curves and $K_d$ values, wherein data points represent the mean±SEM of 5 sample replicates.

To evaluate MDFM performance with common biological assays for quantification, MDFM apparatus and DDFM system results from nanoparticle-based binding affinity and protein quantitation assays were compared. FIG. 7A is a schematic view of a binding affinity assay scheme involving binding between a carboxyl-acid functionalized gold nanorod (AuNR) and an amine modified slide. The nanoparticle binding assay measured the interaction between the carboxylic acid-functionalized gold nanorods (AuNR$^-$) and the amine modified slide, with such interaction being expressed as a function of AuNR$^-$ concentration and the electric field potential at the liquid-solid interface, which obeys Boltzmann statistics.

$$[AuNR^-]_{surface} = [AuNR^-]_{solution} \exp\left(\frac{-e\psi_D}{k_B T}\right) \quad (1)$$

where the amount of AuNR available at the slide surface ([AuNR$^-$]$_{surface}$) was a function of [AuNR$^-$]$_{solution}$, the elementary charge e (1.60218×10$^{-19}$ C), the surface potential $\psi_D$, the Boltzmann constant $k_B$ (1.38066×10$^{-23}$ J/K) and temperature T. This equation simplified to $$[AuNR^-]_{surface} = A[AuNR^-]_{solution} \quad (2)$$

when $\psi_D$ and T were held constant. Based on the Michaelis-Menten model at steady-state, the surface binding rate was described as:

$$\text{Response} = \frac{A[-NH_3^+]_{surface}^{max} \cdot [AuNR^-]}{K_d + [AuNR^-]} \quad (3)$$

determined by the equilibrium binding constant $K_d$, the maximum number of surface binding sites [NH$_3^+$]$_{surface}^{max}$, and the input nanoparticle concentration constant [AuNR$^-$]$_{solution}$, so that $K_d$ can be solved for by curve fitting. We applied this information and concentration-dependent DFM scatter responses from both the MDFM apparatus and DDFM system to calculate the equilibrium binding constant ($K_d$) of this interaction. FIG. 7B provides superimposed plots of response versus nanoparticle concentration (µg/µL) for a binding affinity assay according to the scheme of FIG. 7A obtained using a MDFM apparatus as disclosed herein and a conventional DDFM system, with corresponding nonlinear fitted curves and $K_d$ values, wherein data points represent the mean±SEM of 5 sample replicates. As shown, the MDFM and DDFM response curves produced in this analysis yielded $K_d$ values that did not significantly differ, despite consistently lower MDFM signal throughout the entire range of the AuNR concentration curve.

Figure 8B:
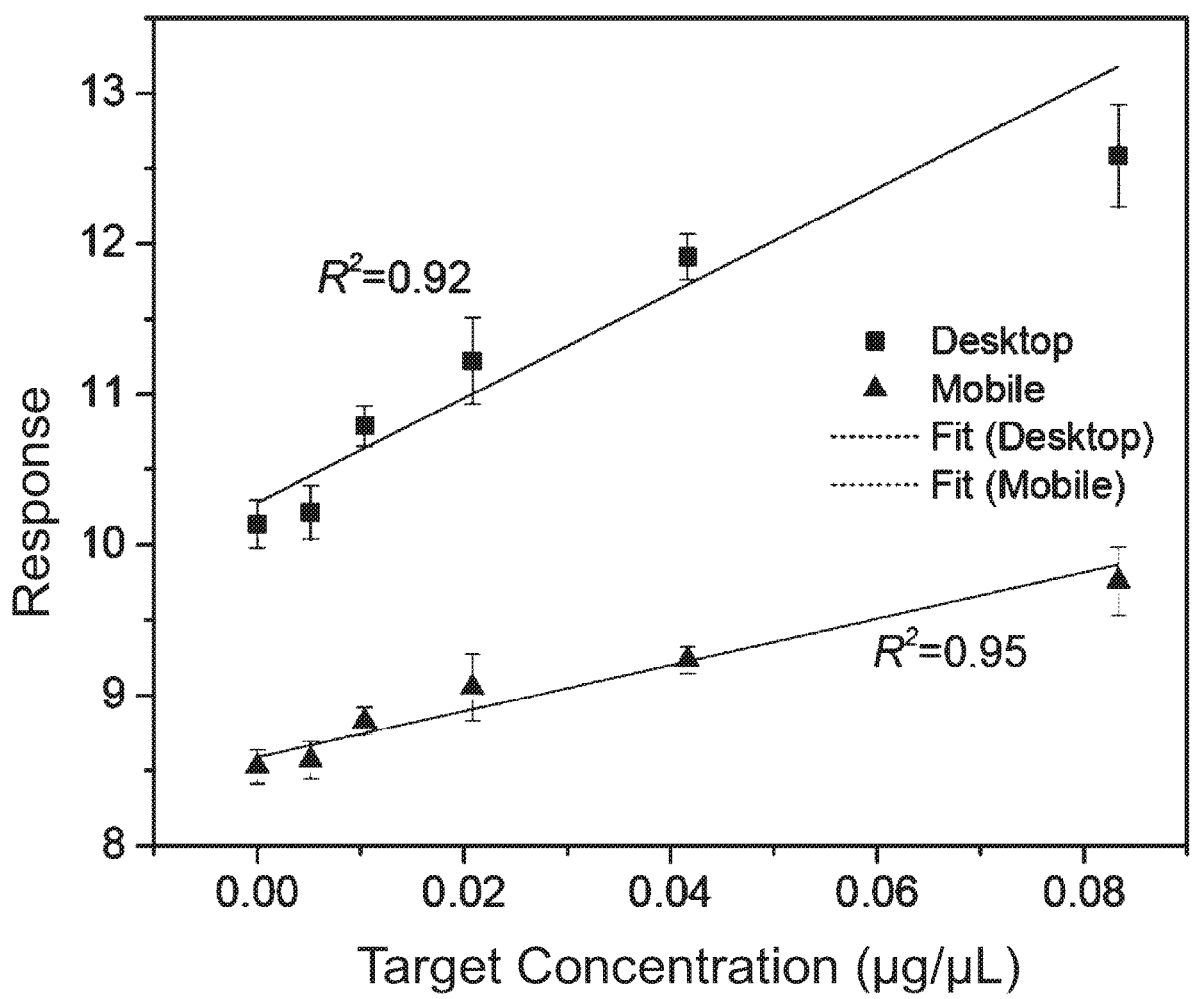
FIG. 8B provides superimposed plots of response versus target concentration (μg/μL) for a protein quantification assay according to the scheme of FIG. 8A obtained using a MDFM apparatus as disclosed herein and a DDFM system, with corresponding linear fits and coefficient of determination ($R^2$) values, and with data points representing the mean±SEM of 5 sample replicates.

Thereafter, MDFM and DDFM performance were analyzed to quantify results of a protein binding assay that used protein A/G-modified slides to capture AuNR-conjugated antibodies. FIG. 8A is a schematic view of a protein quantification assay scheme involving quantification of a biotinylated antibody aCD9 tagged with an avidin modified gold nanoparticle (AuNR) and bound to a protein A/G modified slide. FIG. 8B provides superimposed plots of response versus target concentration (µg/µL) for a protein quantification assay according to the scheme of FIG. 8A obtained using a MDFM apparatus as disclosed herein and a DDFM system, with corresponding linear fits and coefficient of determination ($R^2$) values, and with data points representing the mean±SEM of 5 sample replicates. Both the MDFM and DDFM responses strongly correlated with the target protein concentration; however, the MDFM response exhibited reduced background, less overall variability, and greater linearity than the DDFM response. However, the MDFM apparatus also exhibited a smaller dynamic response over the assay concentration range.

Although gold nanorods are disclosed in certain illustrative embodiments, it is to be appreciated that any suitable nanoparticles providing scatter signals may be used in certain embodiments. Non-limiting examples of nanoparticles providing scatter signals include gold or silver nanoparticles. Other types of nanoparticles may be used.

The reduced dynamic range and/or shallower curves of MDFM signals as compared to DDFM signals in the foregoing assays resulted in higher limits of detection and quantitation for the MDFM-based assays. FIG. 9 is a table identifying sensitivity (including limit of detection (LOD) and limit of quantitation (LOQ) values) for the binding affinity and protein quantification assays described in connection with FIGS. 7A to 8B. The higher limits of detection and quantitation for the MDFM-based assays corresponded to 7-fold and 4.5-fold sensitivity reductions in the binding affinity and protein quantification assays. MDFM assays also revealed less intra-assay and inter-assay precision than DDFM assays, as reflected by increases in intra-assay (0.9- to 3.2-fold) and inter-assay (1.3- to 3.0-fold) coefficient of variation values. However, the MDFM results still revealed reasonable coefficients of variation for both intra-assay (3.1% to 7.8%) and inter-assay (8.1% to 13.7%) replicates.

Lighting induced artifacts observed with the current MFDM prototype prevent its use for obtaining high-quality DFM imagery, but do not decrease its utility for nanoparticle-based quantitation assays once images are processed to correct for artifacts commonly associated with low-magnification far-field DFM images (including uneven lighting and other signal artifacts) using a DFM image processing approach.

Differences in MDFM versus DDFM optical performance appears to derive primarily from reduced DFM signal quality due to weak and uneven sample illumination from a multi-LED light source and non-optimized optics in the exemplary MDFM apparatus disclosed herein. The foregoing issues should be easily addressable through selection of a larger, single-source LED and refining the housing (or implementing other changes), to improve optical focusing to increase DFM image signal quality. Nevertheless, with easy setup and flexible working distance and magnification, the MDFM apparatus disclosed herein was effectively applied for the binding affinity and target protein quantification studies. MDFM apparatuses as disclosed herein are specifically contemplated for hand-held or tabletop use in DFM imaging for bioassay quantitation in resource-limited areas in which it would be impractical or impossible to use conventional DDFM systems.

Those skilled in the art will recognize improvements and modifications to the preferred embodiments of the present disclosure. All such improvements and modifications are considered within the scope of the concepts disclosed herein and the claims that follow.

What is claimed is:

1. A dark-field microscope apparatus comprising:
an adapter housing configured to receive a portable electronic communication device and an objective lens, and to cause the objective lens to be registered with a camera lens of the portable electronic communication device when the portable electronic communication device is received by the adapter housing, wherein the adapter housing comprises a main body and a lens receiver that protrudes from the main body, and the lens receiver is configured to receive the objective lens;
an electrically operated light source;
a dark-field condenser configured to condense light emissions generated by the electrically operated light source;
a slide housing configured to receive at least a portion of an analytical slide and position the analytical slide between the dark-field condenser and the objective lens, wherein the slide housing is configured to receive at least portions of the lens receiver and the objective lens;
a first set screw configured to selectively promote engagement between the lens receiver and either (i) the slide housing or (ii) the objective lens, to permit adjustment of a first distance between the objective lens and the analytical slide; and
a second set screw configured to selectively promote engagement between the slide housing and the dark-field condenser, to permit adjustment of a second distance between the dark-field condenser and the analytical slide.

2. The dark-field microscope apparatus of claim 1, wherein the main body comprises a support surface configured to abut a face of the portable electronic communication device, and the main body comprises at least one lateral wall configured to abut at least one lateral edge of the portable electronic communication device.

3. The dark-field microscope apparatus of claim 1, wherein:
the slide housing comprises a bore;
the lens receiver comprises a first outer wall configured to fit into a first portion of the bore; and
the dark-field condenser comprises a second outer wall configured to fit into a second portion of the bore.

4. The dark-field microscope apparatus of claim 1, further comprising the objective lens.

5. The dark-field microscope apparatus of claim 4, wherein the objective lens, the slide housing, and the dark-field condenser are configured to form an optical path having a center aligned with an emissive center of the electrically operated light source.

6. The dark-field microscope apparatus of claim 5, wherein the slide housing defines at least one slot that is configured to receive the at least a portion of the analytical slide; and the slide housing is configured to permit the analytical slide to move relative to the slide housing to expose a different portion of the analytical slide to the optical path with each movement of the analytical slide.

7. The dark-field microscope apparatus of claim 4, wherein the objective lens provides a magnification in a range of 4 times to 100 times.

8. The dark-field microscope apparatus of claim 4, wherein the objective lens is configured to provide variable magnification.

9. The dark-field microscope apparatus of claim 4, configured to permit the objective lens to be swapped with a different objective lens to provide multiple different magnifications.

10. A biomolecule quantification device comprising the dark-field microscope apparatus of claim 4, wherein the analytical slide is received by the slide housing, and the analytical slide contains at least one nanoparticle-based biomarker.

11. The biomolecule quantification device of claim 10, wherein the at least one nanoparticle-based biomarker comprises at least one gold or silver nanoparticle.

12. A method for performing a biological quantitative study utilizing the dark-field microscope apparatus according to claim 4, the method comprising:
inserting at least a portion of the analytical slide into the slide housing to position the analytical slide between the dark-field condenser and the objective lens, wherein the analytical slide comprises at least one biomolecule and at least one nanoparticle-based biomarker;
transmitting light emissions generated by the electrically operated light source through the dark-field condenser to impinge condensed light emissions on a target region of the at least a portion of the analytical slide; and
generating a magnified image of the target region using the objective lens and the portable electronic communication device received by the adapter housing.

13. A method for diagnosing a disease using the dark-field microscope apparatus according to claim 4, the method comprising:
inserting at least a portion of the analytical slide into the slide housing to expose an area of interest of the analytical slide to an optical path between the dark-field condenser and the objective lens, wherein the area of interest of the analytical slide contains target biomolecules and labels embodying conjugated nanoparticles comprising binding counterparts for the target biomolecules;
transmitting light emissions generated by the electrically operated light source through the dark-field condenser to impinge condensed light on the area of interest of the analytical slide; and
generating a magnified image of the area of interest of the analytical slide using the objective lens and the portable electronic communication device received by the adapter housing; and
analyzing the magnified image.

14. The dark-field microscope apparatus of claim 1, further comprising a base element configured to support the electrically operated light source and configured to receive an end portion of the slide housing.

15. The dark-field microscope apparatus of claim 1, wherein the electrically operated light source comprises a solid state light source.

16. The dark-field microscope apparatus of claim 15, wherein the solid state light source comprises at least one light emitting diode configured to generate a peak wavelength in the visible range.

17. The dark-field microscope apparatus of claim 1, wherein the portable electronic communication device comprises a mobile phone.

18. The dark-field microscope apparatus of claim 1, wherein the adapter housing comprises at least one polymeric material and the slide housing comprises at least one polymeric material.

19. The dark-field microscope apparatus of claim 1, wherein the adapter housing and the slide housing are fabricated by three-dimensional printing.

20. The dark-field microscope apparatus of claim 1, wherein the adapter housing and the slide housing are fabricated by molding.

21. The dark-field microscope apparatus of claim 1, wherein the adapter housing and the slide housing are fabricated by a subtractive material removal process.

\* \* \* \* \*